US00PP10096P

United States Patent [19]

Strangman et al.

[11] Patent Number: Plant 10,096

[45] Date of Patent: Nov. 4, 1997

[54] LITHODORA DIFFUSUM PLANT NAMED 'LITHOSPERMUM STAR'

[75] Inventors: Elizabeth Strangman; Graham Gough, both of Hawkhurst, England

[73] Assignee: Blakedown Nurseries Ltd., Worcester, United Kingdom

[21] Appl. No.: 694,170

[22] Filed: Aug. 8, 1996

[51] Int. Cl.[6] ..... A01H 5/00

[52] U.S. Cl. ..... Plt./54.1

[58] Field of Search ..... Plt./54.1

*Primary Examiner*—James R. Feyrer
*Attorney, Agent, or Firm*—C. A. Whealy

[57] ABSTRACT

A distinct cultivar of Lithospermum plant named 'Litospermum Star', characterized by its unique blue and white bi-color flowers; long-lasting flowers; compact plant habit; long peduncles that hold flowers above foliage; and frost tolerance.

1 Drawing Sheet

The present invention relates to a new and distinct cultivar of Lithospermum plant, botanically known as *Lithodora diffusum,* and hereinafter referred to by the cultivar name 'Lithospermum Star'.

The new cultivar is a naturally-occurring flower color mutation of the nonpatented *Lithodora diffusum* cultivar Heavenly Blue. In 1990, the new cultivar was discovered by the inventors in a controlled environment in Hawkhurst, Kent, England, within a population of plants of the cultivar Heavenly Blue.

In side-by-side comparisons in Hawkhurst, Kent, England, under commercial practice, plants of the new Lithospermum are similar to plants of the cultivar Heavenly Blue in foliage color and plant habit. However plants of the cultivar Heavenly Blue have solid blue flowers whereas plants of the new Lithospermum have blue and white bi-colored flowers.

Asexual reproduction of the new cultivar by terminal cuttings taken at Hawkhurst, Kent, England, has shown that the unique features of this new Lithospermum plant are stable and reproduced true to type in successive generations of asexual reproduction.

The cultivar 'Lithospermum Star' has not been observed under all possible environmental conditions. The phenotype may vary somewhat with variations in environment such as temperature and light intensity, without, however, any variance in genotype.

The following observations, measurements and comparisons describe plants grown in Hawkhurst, Kent, England, under glass with day temperatures ranging from 10 to 15C and night temperatures ranging from 5 to 10C.

The following traits have been repeatedly observed and are determined to be the unique characteristics of 'Lithospermum Star'. These characteristics in combination distinguish 'Lithospermum Star' as a new and distinct cultivar:

1. Unique blue and white bicolor flowers.
2. Long-lasting flowers.
3. Compact plant habit.
4. Long peduncles that hold flowers above foliage.
5. Frost tolerance.

The accompanying colored photographs illustrate the overall appearance of the new cultivar, showing the colors as true as it is reasonably possible to obtain in colored reproduction of this type.

The first photograph comprises a top perspective view of typical plants of the cultivar 'Lithospermum Star'.

The second photograph comprises a close-up view of individual flowers of the cultivar 'Lithospermum Star'.

Flower and foliage colors in the photographs may appear different than the actual colors due to light reflectance.

In the following description, color references are made to The Royal Horticultural Society Colour Chart except where general terms of ordinary dictionary significance are used.

Botanical classification: *Lithodora diffusum* cultivar Lithospermum Star.

Parentage: Naturally-occurring flower color mutation of the nonpatented *Lithodora diffusum* cultivar Heavenly Blue.

Propagation:

*Type cutting.*—Terminal vegetative cuttings.

*Time to initiate and develop roots.*—Summer: About 14 days. Winter: About 28 days.

*Rooting habit.*—Vigorous, numerous, fibrous, and well-branched.

Plant description:

*Form.*—Compact, rounded, spreading herbaceous plant.

*Branching habit.*—Moderate branching, usually two to three lateral branches develop when terminal apex is removed (pinched). Lateral branches are usually 8 to 10 cm in length.

*Plant height.*—20 to 30 cm from soil level to top of plant plane.

*Vigor.*—Moderate.

*Growth rate.*—Slow to moderate.

*Foliage description.*—Leaves small, single, generally symmetrical, and long persisting. Leaves arranged in a rosette. Usually about 20 leaves per lateral branch. Size (largest leaves): Length: About 1.5 cm. Width: About 5 mm. Shape: Oblanceolate. Apex: Acute. Base: Cuneate. Margin: Entire. Texture: Pubescence on abaxial surface. Color: Young and fully expanded leaves: Abaxial surface: 137B. Adaxial surface: 139C.

Flower description:

*Flower type and habit.*—Single, star-shaped flowers that face upwards. Calyx five-parted, petals fused at base. Typically three to six flowers per lateral stem.

*Natural flowering season.*—Spring, typical April through May in the Northern Hemisphere.

*Flower longevity.*—Flowers last four to six weeks on the plant. Flowers persistent.

*Quantity.*—Numerous flowers per plant.

*Flower diameter.*—About 2 cm.

*Flower depth.*—About 1.5 cm.

*Petals.*—Appearance: Velvety. Petal quantity: Five, fused at base. Petal apex: Acute to obtuse. Margin: Entire. Texture: Smooth. Length: About 1 cm. Width:

About 5 mm. Color: Abaxial surface: 111A center with white margin. With subsequent development, center color fades slightly to 113A. Adaxial surface: 115A.

*Peduncle.*—Aspect: Upright. Strength: Flexible. Length: About 12 cm. Texture: Pubescent. Color: 145B.

*Flower bud.*—Shape: Elongated. Rate of opening: 3 to 4 days. Length: 1 to 1.5 cm. Diameter: About 5 mm. Color: 115A.

*Calyx.*—Shape: Funnel. Diameter: About 1.5 cm. Texture: Glabrous. Color: 113A.

*Reproductive organs.*—Stamen number: One. Pistil number: One. Ovary Number: Three.

Disease resistance: Similar to other Lithospermums, the new Lithospermum is susceptible to Botrytis infection.

Seed production: Seed production is not typically observed.

It is claimed:

1. A new and distinct cultivar of Lithospermum plant named 'Lithospermum Star', as illustrated and described.

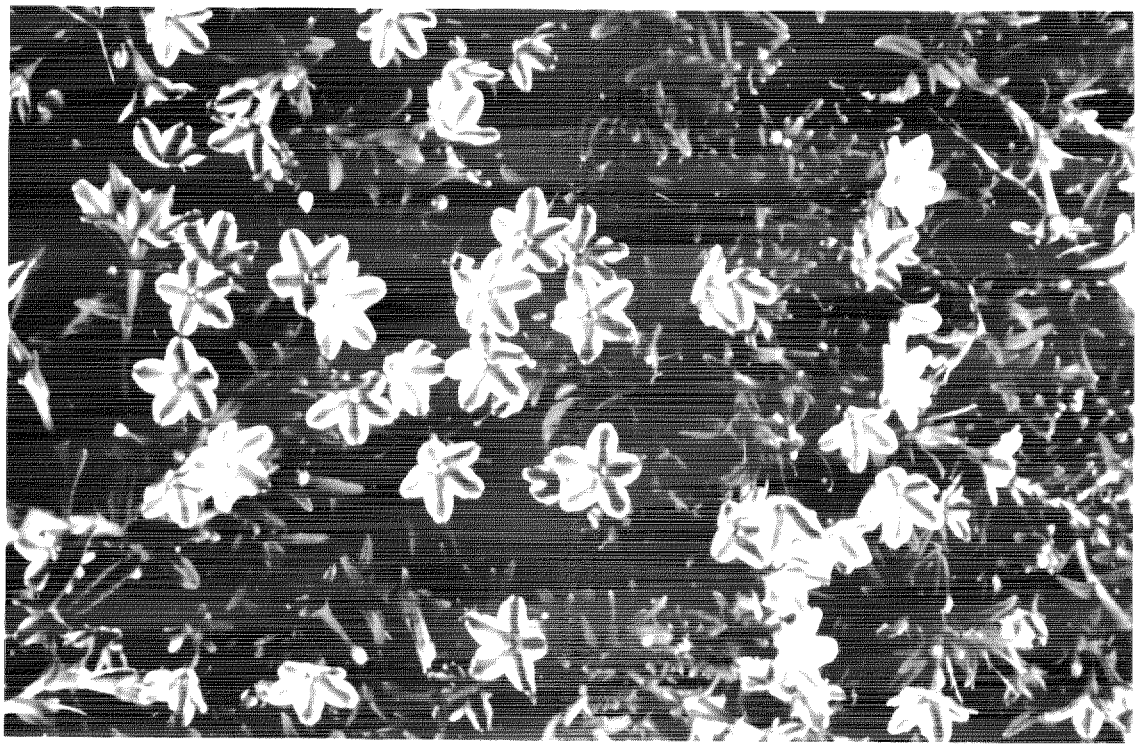
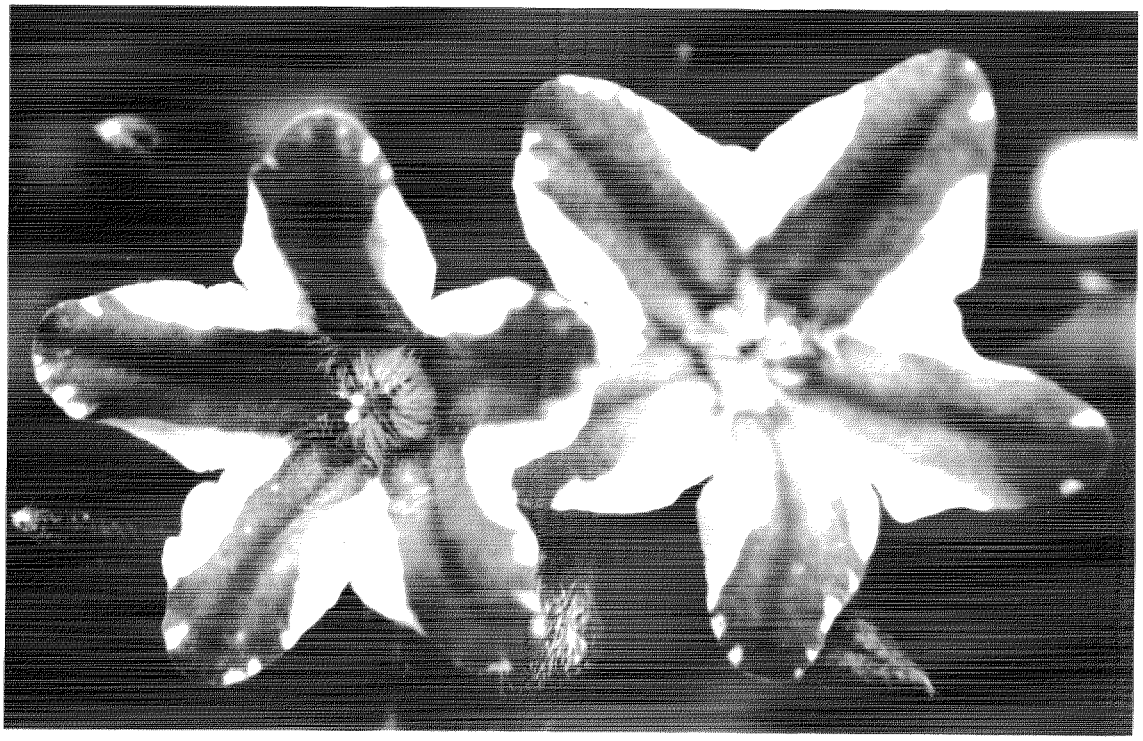

* * * * *